United States Patent
Kim et al.

(10) Patent No.: US 8,199,325 B2
(45) Date of Patent: Jun. 12, 2012

(54) APPARATUS FOR DETECTING BIOMATERIALS AND METHOD FOR DETECTING BIOMATERIALS BY USING THE APPARATUS

(75) Inventors: Wanjoong Kim, Goyang-si (KR); Chul Huh, Daejeon (KR); Hyunsung Ko, Seoul (KR); Kyung Hyun Kim, Daejeon (KR); Gun Yong Sung, Daejeon (KR); Seon Hee Park, Daejeon (KR); Bong Kyu Kim, Daejeon (KR); Chil Seong Ah, Daejeon (KR); Ansoon Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 501 days.

(21) Appl. No.: 12/534,464

(22) Filed: Aug. 3, 2009

(65) Prior Publication Data

US 2010/0141942 A1    Jun. 10, 2010

(30) Foreign Application Priority Data

Dec. 10, 2008  (KR) .................. 10-2008-0125336
Apr. 22, 2009  (KR) .................. 10-2009-0035121

(51) Int. Cl.
*G01N 21/55*    (2006.01)

(52) U.S. Cl. ...................................... 356/445; 356/448

(58) Field of Classification Search .......... 356/445–448, 356/450–458
See application file for complete search history.

(56) References Cited

U.S. PATENT DOCUMENTS

| | | | | |
|---|---|---|---|---|
| 6,579,721 | B1 * | 6/2003 | Natan et al. ................. | 436/164 |
| 7,057,732 | B2 * | 6/2006 | Jorgenson et al. ........... | 356/445 |
| 8,105,822 | B2 * | 1/2012 | Goodrich ................... | 435/287.9 |

FOREIGN PATENT DOCUMENTS

| KR | 1020030064992 | 8/2003 |
|---|---|---|
| KR | 1020050073609 | 7/2005 |
| KR | 1020070105568 | 10/2007 |

* cited by examiner

*Primary Examiner* — Gregory J Toatley
*Assistant Examiner* — Jarreas C Underwood
(74) *Attorney, Agent, or Firm* — Nelson Mullins Riley & Scarborough LLP; EuiHoon Lee, Esq.

(57) ABSTRACT

Provided are an apparatus and method for detecting biomaterials. The apparatus for detecting the biomaterials includes a light source unit, a biomaterial reacting unit, and a detection unit detecting. The light source unit provides incident light. The biomaterial reacting unit includes a substrate and metal nanoparticles spaced from the substrate. The surface plasmon resonance phenomenon is induced on surfaces of the metal nanoparticles by the incident light. First detecting molecules specifically binding to target molecules are immobilized to the surfaces of the metal nanoparticles. The detection unit detects a resonance wavelength of emission light emitted from the metal nanoparticles by the surface plasmon resonance phenomenon.

20 Claims, 6 Drawing Sheets

APPARATUS FOR DETECTING BIOMATERIALS AND METHOD FOR DETECTING BIOMATERIALS BY USING THE APPARATUS

CROSS-REFERENCE TO RELATED APPLICATIONS

This U.S. non-provisional patent application claims priority under 35 U.S.C. §119 of Korean Patent Application Nos. 10-2008-0125336, filed on Dec. 10, 2008, and 10-2009-0035121, filed on Apr. 22, 2009, the entire contents of which are hereby incorporated by reference.

BACKGROUND OF THE INVENTION

The present invention disclosed herein relates to an apparatus and method for detecting biomaterials, and more particularly, to an apparatus and method for detecting biomaterials using gold nanoparticles.

Apparatuses for detecting biomaterials, i.e., biosensors are devices capable of detecting an optical or electrical signal that varies with the selective reaction and combination between a biological receptor recognizing specific biomaterials contained in a biological tissue such as blood or urination and an analyte to be analyzed. That is, biosensors can detect the existence of specific biomaterials, or analyze biomaterials qualitatively or quantitatively. Here, the biological receptor (i.e., detection material) includes enzyme, antibody, DNA, etc., which can selectively react and bind to a specific material. To detect a signal, biomaterials are detected and analyzed by using various physicochemical methods, for example, a method of detecting a change in electrical signal according to whether an analyte exists or not, or a method of detecting a change in an optical signal caused by chemical reaction between a receptor and an analyte.

Among the biosensors, a surface plasmon biosensor that detects an optical signal change to analyze biomaterials, a total internal reflection ellipsometry biosensor, and a waveguide biosensor are actively being researched and developed.

SUMMARY OF THE INVENTION

The present invention provides an apparatus that more easily detect biomaterials.

The present invention also provides a method that can more easily detect biomaterials.

The subject of the present invention is not limited to the aforesaid, but other subjects not described herein will be clearly understood by a person with ordinary in the art from descriptions below.

Embodiments of the present invention provide apparatuses for detecting biomaterials including a light source unit providing incident light; a biomaterial reacting unit including a substrate and metal nanoparticles spaced from the substrate; and a detection unit detecting a resonance wavelength of emission light emitted from the metal nanoparticles by a surface plasmon resonance phenomenon, wherein the surface plasmon resonance phenomenon is induced on surfaces of the metal nanoparticles by the incident light, and first detecting molecules specifically binding to target molecules are immobilized to the surfaces of the metal nanoparticles.

In other embodiments of the present invention, methods for detecting biomaterials include: immobilizing first detecting molecules to surfaces of metal nanoparticles having fluidity; irradiating incident light onto the metal nanoparticles to induce a surface plasmon resonance phenomenon and detect a first resonance wavelength of emission light emitted from the metal nanoparticles; specifically binding target molecules to the first detecting molecules immobilized to the metal nanoparticles; irradiating the incident light onto the metal nanoparticles to which the target molecules are immobilized to induce the surface plasmon resonance phenomenon and detect a second resonance wavelength of the emission light emitted from the metal nanoparticles; and comparing the first resonance wavelength to the second resonance wavelength to analyze the target molecules.

In still other embodiments of the present invention, methods for detecting biomaterials include: preparing a buffer solution in which metal nanoparticles to which first detecting molecules are immobilized are dispersed; preparing a substrate to which second detecting molecules are immobilized to a surface thereof; specifically binding target molecules to the second detecting molecules; supplying the buffer solution to the substrate to specifically bind the target molecules to the first detecting molecules; irradiating incident light onto the metal nanoparticles to induce a surface plasmon resonance phenomenon; and detecting a resonance wavelength of emission light emitted from the metal nanoparticles by the surface plasmon resonance phenomenon and varied according to the specific binding between the target molecules and the first detecting molecules.

Details of other example embodiments are included in the detailed description and drawings.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures.

DETAILED DESCRIPTION OF PREFERRED EMBODIMENTS

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the present disclosure, the technical terms are used only for explaining a specific exemplary embodiment while not limiting the present invention. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components.

Additionally, the embodiment in the detailed description will be described with sectional and/or plan views as ideal exemplary views of the present invention. In the drawings, the dimensions of layers and regions are exaggerated for clarity of illustration. Therefore, areas exemplified in the drawings have general properties, and are used to illustrate a specific shape of a semiconductor package region. Thus, this should not be construed as limited to the scope of the present invention.

In the present disclosure, target molecules, which are biomaterials to be analyzed, may be interpreted as analytes.

In the present disclosure, detection molecules, which are biomolecules specifically binding to target molecules, may be interpreted as probe molecules, receptors, or acceptors.

In the present disclosure, a metal nanoparticle denotes a metal particle having a nano-size greater than about 1 nm and less than about 1000 nm. That is to say, the metal nanoparticle has a diameter greater than 1 nm and less than about 1000 nm in embodiments of the present invention.

Hereinafter, an apparatus for detecting biomaterials according to an embodiment of the present invention will be described in detail with reference to drawings.

Figure 1:
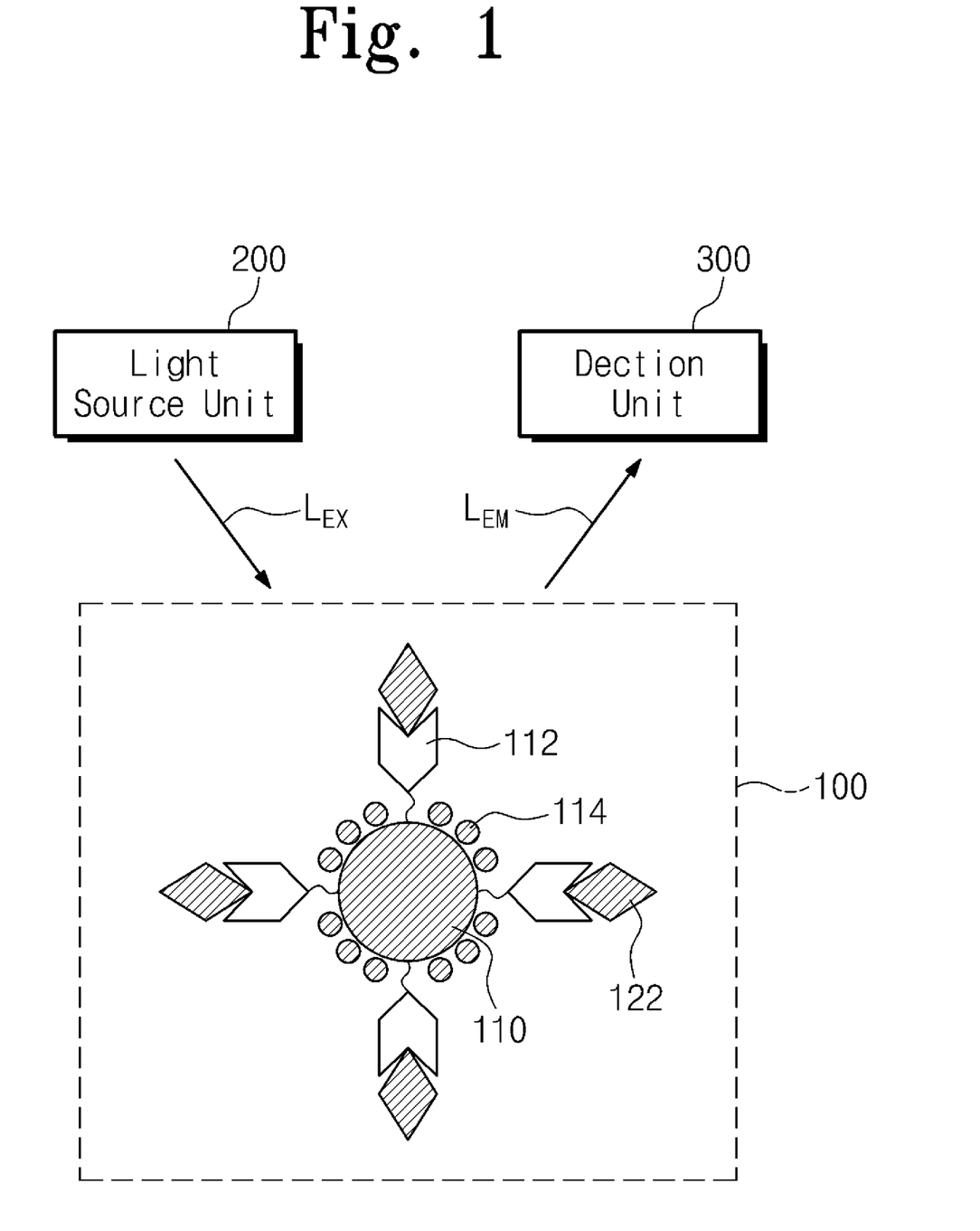
FIG. 1 is a view of an apparatus for detecting a biomaterial according to an embodiment of the present invention.

FIG. 1 is a view of an apparatus for detecting a biomaterial according to an embodiment of the present invention.

Referring to FIG. 1, an apparatus for detecting biomaterials includes a biomaterial reacting unit 100, a light source unit 200, and a detection unit 300.

The biomaterial reacting unit 100 includes metal nanoparticles 110 for analyzing target molecules 122. The biomaterial reacting unit 100 may include a chamber that can store fluid (for example, blood, serum, blood plasma, or urine) used for detecting biomaterials.

A surface plasmon phenomenon occurs by an electromagnetic wave (i.e., energy or wavelength) applied from the outside in the metal nanoparticles.

The surface plasmon phenomenon refers to the quantized oscillation of electrons caused by the polarization of the electrons existing inside the metal nanoparticles 110 when light of a specific wavelength is irradiated onto surfaces of the metal nanoparticles 110.

When the light of the specific wavelength is incident onto the metal nanoparticles 110 at a specific angle, the light may be absorbed and scattered by the metal nanoparticles 110 to cause a surface plasmon resonance phenomenon in which plasmon of the surfaces of the metal nanoparticles 110 is excited. When the surface plasmon resonance phenomenon occurs, the light incident onto the metal nanoparticles 110 is absorbed into the metal nanoparticles 110, and light of a specific wavelength (i.e., resonance wavelength) is scattered according to an ambient material surrounding the surfaces of the metal nanoparticles 110. Also, when the surface plasmon resonance phenomenon occurs, the resonance wavelength may be different according to a kind, composition, size, shape of the metal nanoparticles 110 and the ambient material surrounding the surfaces of the metal nanoparticles 110. Thus, when the surface plasmon resonance phenomenon occurs, a resonance wavelength of the emission light emitted from the metal nanoparticles 110 may be analyzed to detect whether the biomaterials exist and a concentration of the biomaterials.

In embodiments of the present invention, by using the metal nanoparticles 110, when incident light $L_{EX}$ of a specific wavelength for generating the surface plasmon resonance is irradiated, the surface plasmon resonance phenomenon may occur on the surfaces of the metal nanoparticles 110 without reference to an incident angle of the incident light.

The metal nanoparticles 110 may include a noble metal of which a dielectric function has a minus imaginary part, for example, gold (Au) or silver (Ag).

In the biomaterial reacting unit 100, the metal nanoparticles 110 may exist in a buffer solution such as water or phosphate buffered saline (PBS) solution.

First detecting molecules 112 specifically binding to target molecules 122 are immobilized by a chemical method on the surfaces of the metal nanoparticles 110. In an embodiment of the present invention, protein molecules such as an albumin antibody for diagnosing kidney diseases, an N-telopeptide antibody (that is a bone metabolism marker) for diagnosing osteoporoses, a deoxy-pyridinoline antibody, an antibody for diagnosing prostate cancer, and an anti-prostate specific antigen (anti-PSA) antibody may be used as the first detecting molecules 112. The first detecting molecules 112 may be achieved from blood, serum, blood plasma, or urine.

The first detecting molecules 112 may be immobilized to the surfaces of the metal nanoparticles 110 by chemical adsorption, covalent-binding, electrostatic attraction, copolymerization, or avidin-biotin affinity system.

A functional group may be derived to more strongly immobilize the first detecting molecules 112 to the surfaces of the metal nanoparticles 110. For example, a functional group such as a carboxyl group (—COOH), a thiol group (—SH), a hydroxyl group (—OH), a silane group, amine group, or an epoxy group may be derived to the surfaces of the metal nanoparticles 110.

Casein 114 may be immobilized to the surfaces of the metal nanoparticles 110. The casein 114 serves as blocking molecules for preventing a nonspecific binding of the target molecules 122 together with the first detecting molecules 112.

When the target molecules 122 are provided to the metal nanoparticles 110 to which the first detecting molecules 112 are immobilized to the surfaces thereof, the target molecules 122 may specifically bind to the first detecting molecules 112 and immobilized around the metal nanoparticles 110. An albumin antigen, an N-telopeptide antigen, a deoxy-pyridinoline antigen, a prostate specific antigen may be used as the target molecules 122. The target molecules 122 may specifically bind to the first detecting molecules 112 by an immune reaction.

Since the first detecting molecules 112 specifically bind to the target molecules 122 on the surfaces of the metal nanoparticles 110, the resonance wavelength of the scattered light emitted from the surfaces of the metal nanoparticles 110 may be varied by incident light of a specific wavelength incident onto the metal nanoparticles 110.

In another embodiment of the present invention, the first detecting molecules 112 and the target molecules 122 may include protein, cell, virus, nucleic acid, organic molecule or inorganic molecule. The protein may include any biomaterial such as antigen, antibody, matrix protein, enzyme, and coenzyme. The nucleic acid may include DNA, RNA, PNA, LNA, or hybrids thereof.

The light source unit 200 irradiates incident light of a specific wavelength onto the metal nanoparticles 110 of the biomaterial reacting unit 100. The incident light irradiated onto the biomaterial reacting unit 100 is absorbed into and scattered by the surfaces of the metal nanoparticles 110.

A xenon lamp outputting polychromatic light may be used as the light source unit 200. In case where the xenon lamp is used as a light source, the light source unit 200 further includes an optical filter to provide monochromatic light having a wavelength corresponding to the plasmon resonance wavelength of the metal nanoparticle 110 to the target molecules 122. A laser diode outputting monochromatic light having a specific wavelength may be used as the light source unit 200. Alternatively, a white light source or a light-emitting diode (LED) may be used as the light source unit 200.

The detection unit 300 detects a wavelength of emission light emitted from the surfaces of the metal nanoparticles 110. That is, when the surface plasmon resonance phenomenon occurs, the detection unit 300 detects the emitted surface plasmon resonance wavelength. An UV spectrometer may be used as the detection unit 300. The UV spectrometer may detect absorbance of light having a wide wavelength band. That is, the detection unit 300 may detect the surface plasmon resonance wavelength changed according to the specific binding between the metal nanoparticles 110 and the target molecules 122. Also, the detection unit 300 may analyze the change of the surface plasmon resonance wavelength to quantify the concentration of the biomaterials to be analyzed.

Figure 2A:
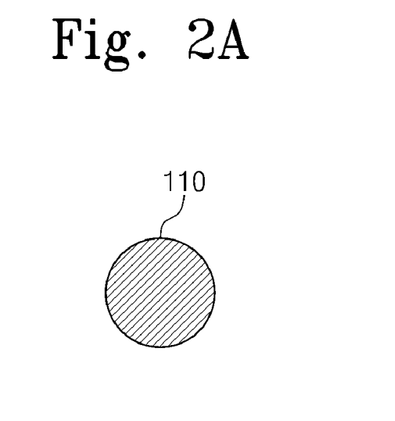
FIGS. 2A to 2C are views of a method for detecting a biomaterial according to an embodiment of the present invention.
Figure 2B:
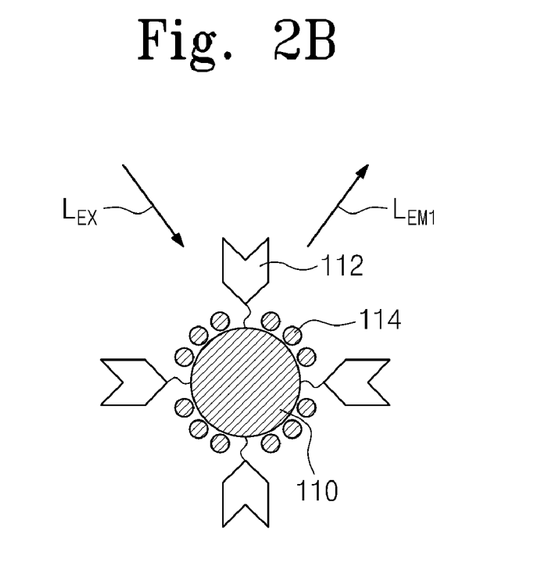
Figure 2C:
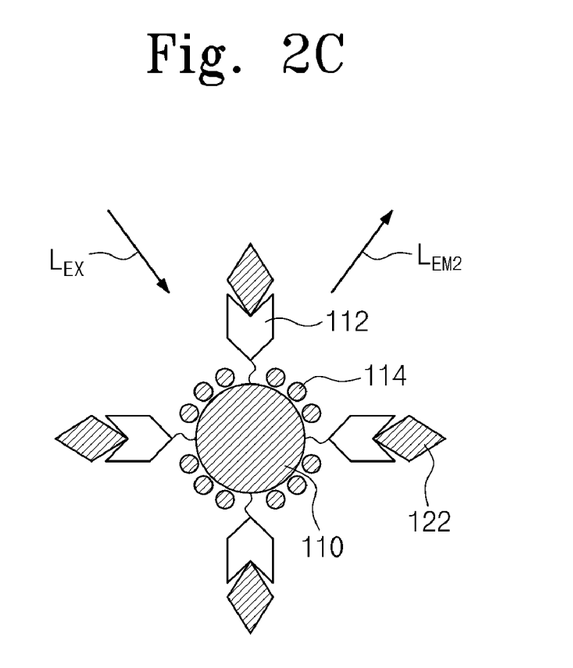

FIGS. 2A to 2C are views of a method for detecting a biomaterial according to an embodiment of the present invention.

Referring to FIG. 2A, metal nanoparticles 110 are manufactured. For example, the metal nanoparticles 110 may be manufactured in nano-scale using a physical, chemical, or electrolysis method. To detect biomaterials, a metal colloid solution in which the metal nanoparticles 110 are dispersed in a buffer solution is prepared. That is, the metal colloid solution may be prepared in a biomaterial reacting unit (see reference numeral 100 of FIG. 1).

Referring to FIG. 2B, first detecting molecules 112 are immobilized to surfaces of the metal nanoparticles 110. In this embodiment, gold nanoparticles having diameters of about 10 nm may be used as the metal nanoparticles 110. Polyclonal albumin antibodies may be used as the first detecting molecules 112.

In detail, to immobilize the polyclonal albumin antibodies, a $K_2CO_3$ solution may be supplied into the gold colloid solution to adjust its acidity. Thus, the acidity of the gold colloid solution may be adjusted to about pH 9. Particularly, in order to adjust acidity of the gold colloid solution of about 1 mL to about pH 9, about 10 µL of the $K_2CO_3$ solution is supplied to mix the gold colloid solution with the $K_2CO_3$ solution while the mixed solution is shaken for about one minute. Then, about 36 µL of albumin is supplied into the gold colloid solution while the albumin is quickly shaken to react at about 20° C. for about 30 minutes. In this case, about 27 first detecting molecules 112 may be immobilized to one gold nanoparticle 110.

Thereafter, about 100 µL of a casein solution is supplied to react again for about 30 minutes, thereby inhibiting an nonspecific reaction on the gold nanoparticles 110 and inducing a selective immune reaction.

The above reaction solution is centrifugal-separated at about 1200 rpm for about 20 minutes to remove the remaining albumin and casein that are not immobilized to the gold nanoparticles 110. Thereafter, about 1 mL of 0.5% casein solution is additionally supplied, and the resultant solution is centrifugal-separated again. This process may be repeated more than two times.

An initial surface plasmon resonance wavelength emitted from the gold nanoparticles 110 to which the first detecting molecules 112 are immobilized to the surfaces thereof, i.e., a first resonance wavelength is measured. That is, incident light $L_{EX}$ having a specific wavelength is irradiated onto the gold nanoparticles 110 to which only the first detecting molecules 112 is immobilized therearound, and emission light $L_{EM1}$ emitted from the gold nanoparticles 110 is detected using an UV spectrometer. Since the incident light $L_{EX}$ having the specific wavelength is incident onto the gold nanoparticles 110, the incident light $L_{EX}$ may be absorbed into and scattered by the surfaces of the gold nanoparticles 110 to measure the first resonance wavelength.

Referring to FIG. 2C, albumin that is target molecules 122 is supplied to the gold nanoparticles 110 to which the first detecting molecules 112 are immobilized to the surfaces thereof. Thus, the first detecting molecules 112 may specifically bind to the target molecules 122 on the surfaces of the gold nanoparticles 110.

The incident light $L_{EX}$ is irradiated onto the gold nanoparticles 110 in which the first detecting molecules 112 and the target molecules 122 specifically bind to each other, and emission light $L_{EM2}$ emitted from the gold nanoparticles 110 is detected again using the UV spectrometer. As a result, a surface plasmon resonance wavelength according to the specific binding of the target molecules 122, i.e., a second resonance wavelength may be measured. In this case, the resonance wavelength may be moved from the first resonance wavelength to the second resonance wavelength due to the specific binding of the target molecules 122.

That is, before and after the first detecting molecules 112 specifically bind to the target molecules, a resonance wavelength change of the surface plasmon emitted from the gold nanoparticles 110 may be analyzed to detect the target molecules 122 and quantify a concentration of the target molecules 122.

Figure 3:
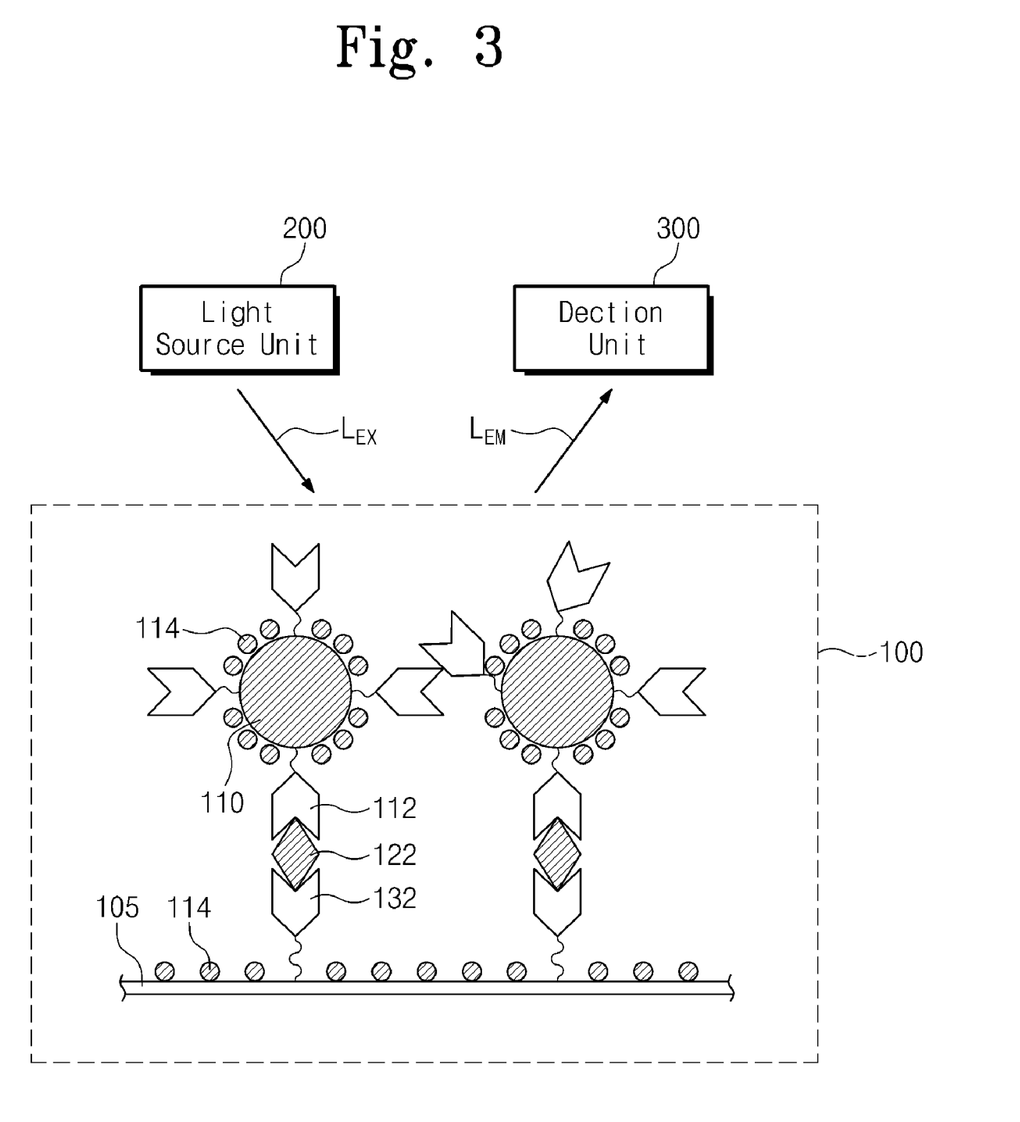
FIG. 3 is a view of an apparatus for detecting a biomaterial according to another embodiment of the present invention.

Hereinafter, an apparatus for detecting a biomaterial according to another embodiment of the present invention will be described with reference to FIG. 3. This embodiment will be described mainly in detail on only different points from the aforementioned embodiment. FIG. 3 is a view of an apparatus for detecting a biomaterial according to another embodiment of the present invention.

Referring to FIG. 3, an apparatus for detecting biomaterials includes a biomaterial reacting unit 100, a light source unit 200, and a detection unit 300.

The biomaterial reacting unit 100 includes a substrate 105 to which a second detecting molecules 132 specifically binding to target molecules 122 are immobilized. The target molecules 122 may specifically bind to first detecting molecules 112 and the second detecting molecules 132 on the substrate due to a sandwich immune reaction. The first detecting molecules 112 are immobilized to surfaces of metal nanoparticles 110. Thus, a conjugate of the second detecting molecule 132, the target molecule 122, the first detecting molecule 112, and the metal nanoparticle 110 may be formed on the substrate 105 in this embodiment.

In this embodiment, the substrate 105 may be a portion of a microfluidic channel. For example, the substrate 105 may include one of a plastic substrate, a glass substrate and a silicon substrate. Also, the substrate 105 may be formed of a polymer such as polydimethylsiloxane (PDMS), polymethylmethacrylate (PMMA), polycarbonate (PC), cyclic olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutylene-terephthalate (PBT), fluorinated ethylenepropylene (FEP), and perfluoralkoxyalkane (PFA).

The first and second detecting molecules 112 and 132 include a plurality of binding sites to which the target molecules 122 bind. In the first and second detecting molecules 112 and 132, the binding sites to which the target molecules 122 bind have characteristics different from each other. In this embodiment of the present invention, the second detecting molecules 132 may include monoclonal antibodies, and the first detecting molecules 112 may include polyclonal antibodies.

The first detecting molecules 112 may be immobilized to the surfaces of the metal nanoparticles 110 and provided into the biomaterial reacting unit 100. Caseins 114 may be immobilized to the surfaces of the metal nanoparticles 110 to prevent the target molecules 122 from nonspecifically binding.

That is, the antibodies and the metal nanoparticles 110 are provided into the biomaterial reacting unit 100, and the sandwich immune reaction between the second detecting molecules 132, the target molecules 122, and the first detecting molecules 112 may occur on the substrate 105.

Figure 4A:
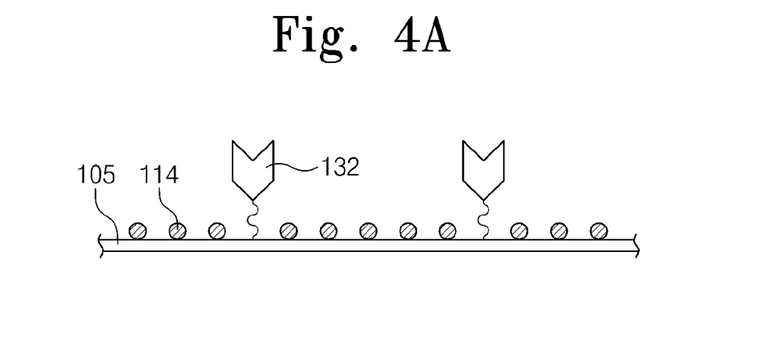
FIGS. 4A to 4C are views of a method for detecting a biomaterial according to another embodiment of the present invention.
Figure 4B:
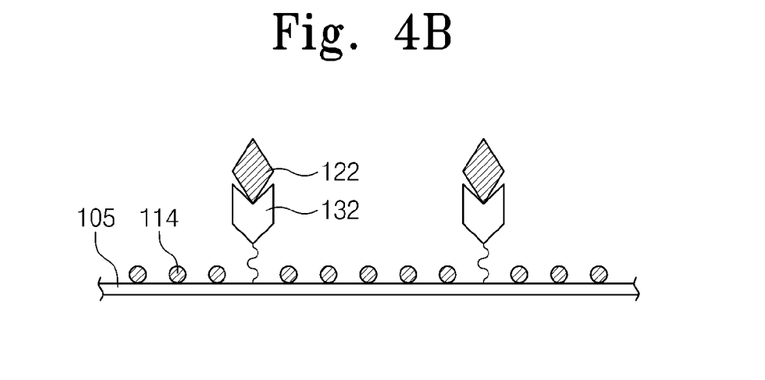
Figure 4C:
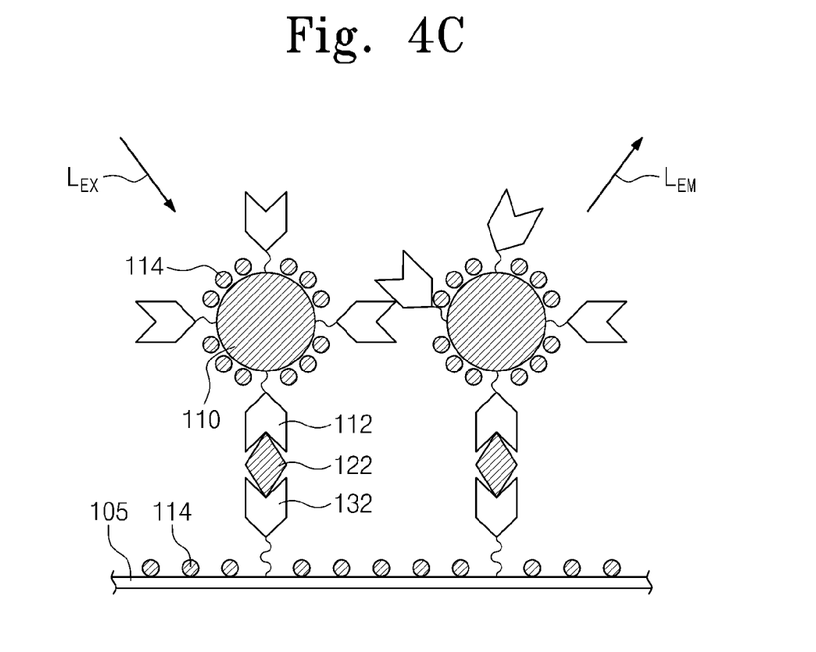

FIGS. 4A to 4C are views of a method for detecting a biomaterial according to another embodiment of the present invention. In this embodiment, monoclonal albumin antibodies are used as the second detecting molecules 132, and polyclonal albumin antibodies are used as the first detecting molecules 112.

Referring to FIG. 4A, the silicon substrate 105 is prepared. The second detecting molecules 132 are immobilized to a surface of the silicon substrate 105. At this time, the surface of the silicon substrate 105 may have a structure in which the second detecting molecules 132 can be easily immobilized to the surface thereof. In addition, the surface of the silicon substrate 105 may have a structure that has uniform spatial distribution and surface orientation, and can easily functionalize the surface thereof. As a result, the second detecting molecules 132 may be immobilized to the surface of the silicon substrate 105 using linkers. A self-assembled monolayer (SAM), polyethylene glycol (PEG), dextran, or protein G may be used as the linkers. Also, a functional group such as a carboxyl group (—COOH), a thiol group (—SH), a hydroxyl group (—OH), a silane group, amine group, or an epoxy group may be derived to the surface of the silicon substrate 105.

A method in which the monoclonal albumin antibodies 132 are immobilized to the surface of the silicon substrate 105 using the protein G will be described as example in this embodiment.

The method may be performed according to following processes. First, the silicon substrate 105 is sequentially immersed in an acetone solution and a methanol solution to respectively heat the solutions for about 5 minutes. Thereafter, the silicon substrate 105 is washed using an ethanol solution to dry the washed substrate 105 using $N_2$ gas.

Next, the silicon substrate 105 is immersed in the acetone solution, and $O_2$ plasma ashing process is performed for about 5 minutes to form the hydroxyl group (—OH) on the surface of the silicon substrate 105.

Next, the silicon substrate 105 to which the hydroxyl group (—OH) is derived is immersed in an ethanol solution in which about 1% (3-aminopropyl)triethoxy silane (APTES) is dispersed to react for about 30 minutes. Thereafter, the silicon substrate 105 is washed and dried. Then, the silicon substrate 105 may be baked at about 120° C. for about 10 minutes.

Next, the silicon substrate 105 is spotted with about 0.1 mL of a dimethyl sulfoxide (DMSO) solution in which about 0.4 mg of succinmidyl 4-[p-maleimidophenyl]butyrate (SMPB) is dissolved to keep the spotted substrate 105 at about 20° C. for about three hours. After about three hours, the silicon substrate 105 is washed using DMSO and ethanol to dry the washed substrate 105 using the $N_2$ gas.

Next, the silicon substrate 105 is immersed in about 0.1 mg/mL of a protein G solution and kept at about 20° C. for about one hour. Then, the silicon substrate 105 is immersed in phosphate-buffered saline with tween 20 (PBST) (10 mL PBS, 0.2% Tween 20 (pH 7.4)) solution for about 10 minutes, and then, the silicon substrate is washed using PBS (ph 7.4) solution. Thus, the protein G may be immobilized to the hydroxyl group (—OH).

Next, the silicon substrate 105 to which the protein G is derived is spotted with about 0.2 mg/mL of a monoclonal albumin antibody solution. Then, the spotted substrate 105 is kept at about 20° C. for about two hours. Thereafter, the silicon substrate 105 is washed using a PBST (10 mL PBS, 0.5% Tween 20 (pH 7.4)) solution and the PBS (pH 7.4) solution. Thus, the monoclonal albumin antibodies 132 may be immobilized to the surface of the silicon substrate 105 by the protein G.

Next, the silicon substrate 105 to which the monoclonal albumin antibodies 132 is immobilized is immersed in 0.3% BSA solution at about 20° C. for about one hour. Thereafter, the silicon substrate 105 is washed using the PBS (pH 7.4) solution.

Referring to FIG. 4B, the target molecules 122 specifically bind to the substrate 105 to which the second detecting molecules 132 are immobilized to the surface thereof.

In detail, a solution in which the albumin that is the target molecules 122 is dispersed is supplied to the substrate 105 to keep the substrate 105 at room temperature for a predetermined time. As a result, the albumin 122 specifically binds to the monoclonal albumin antibodies 132. The substrate 105 is washed using distilled water to remove the albumin 122 that does not bind to the monoclonal albumin antibodies 132. As a result, the target molecules 122 may be immobilized to the substrate 105.

Referring to FIG. 4C, the target molecules 122 immobilized to the substrate 105 specifically bind to the first detecting molecules 112 immobilized to the surfaces of the gold nanoparticles 110.

In detail, a colloid solution in which the gold nanoparticles 110 are dispersed is prepared. At this time, the polyclonal albumin antibodies 112 that are the first detecting molecules 112 were immobilized to the surfaces of the gold nanoparticles 110. To immobilize the polyclonal albumin antibodies 112 to the surfaces of the gold nanoparticles 110 was described with reference to FIGS. 2A and 2B.

The colloid solution in which the gold nanoparticles 110 to which the first detecting molecules 112 are immobilized are dispersed is supplied to the substrate 105 to which the second detecting molecules 132 and the target molecules 122 are immobilized. Thereafter, the target molecules 122 react with the first detecting molecules 112 for a predetermined time.

After the predetermined time passes, the substrate 105 is washed using distilled water to remove the gold nanoparticles that do not specifically bind to the target molecules 122. Thus, a conjugate of the second detecting molecule 132, the target molecule 122, the first detecting molecule 112, and the gold nanoparticle 110 may be immobilized to the substrate 105. That is, whether the target molecules 122 specifically bind may be determined according to whether the gold nanoparticles 100 are immobilized to the substrate 105.

Incident light $L_{EX}$ is irradiated onto the substrate 105 in which the gold nanoparticles 110 are immobilized by the specific binding between the target molecules 122 and the first detecting molecules 112, and emission light $L_{EM}$ emitted from the gold nanoparticles 110 is detected using an ultraviolet (UV) spectrometer. As a result, a surface plasmon resonance phenomenon occurs at the gold nanoparticles 110 by the incident light $L_{EX}$ to measure a resonance wavelength according to the specific binding of the target molecules 122.

In this embodiment, the target molecules 122 may be detected according to whether the gold nanoparticles 100 are immobilized to the substrate 105. Also, a change of the resonance wavelength of the emission light $L_{EM}$ emitted from the surfaces of the gold nanoparticles 110 may be analyzed to detect a concentration of the target molecules 122.

Figure 5:
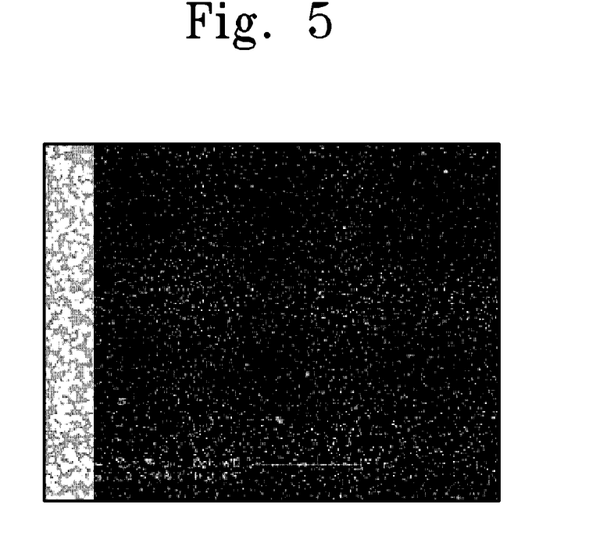
FIG. 5 is a field emission-scanning electron microscope (FE-SEM) image of gold nanoparticles immobilized to a substrate by a sandwich immune reaction according to another embodiment of the present invention.

FIG. 5 is a field emission-scanning electron microscope (FE-SEM) image of gold nanoparticles immobilized to a substrate by a sandwich immune reaction according to another embodiment of the present invention.

The FE-SEM image of FIG. 5 was photographed after following processes are performed. The albumin is provided to the substrate 105 to which the monoclonal albumin antibodies are immobilized to react with each other. Thereafter, the gold nanoparticles to which the polyclonal albumin antibodies are immobilized to the surfaces thereof are provided to react with each other. Referring to FIG. 5, the gold nanoparticles are attached to the substrate with the density of about 400 EA/$\mu m^2$. That is, it may confirm that the gold nanoparticles are attached to the substrate through FIG. 5. That is to say, it may confirm that the sandwich immune reaction occurs between the monoclonal albumin antibodies, the albumin, and the polyclonal albumin antibodies.

Figure 6A:
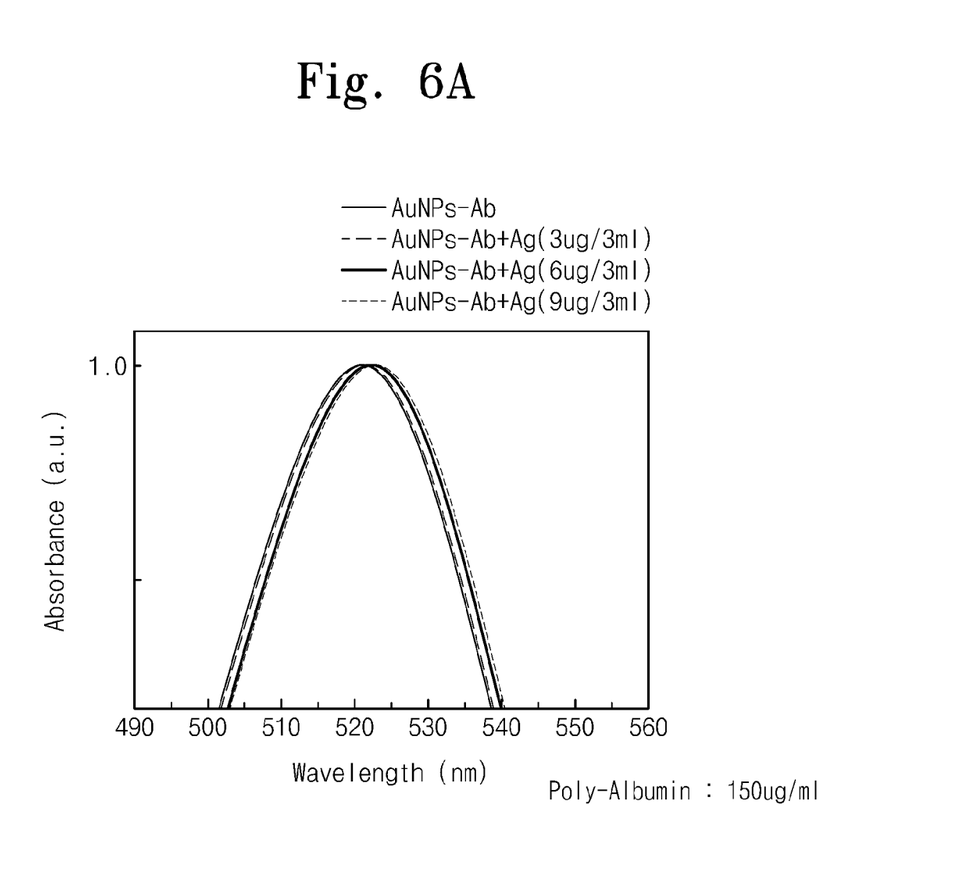
FIG. 6A is a graph illustrating a change of a resonance wavelength according to a concentration change of target molecules supplied to a substrate in another embodiment of the present invention.
Figure 6B:
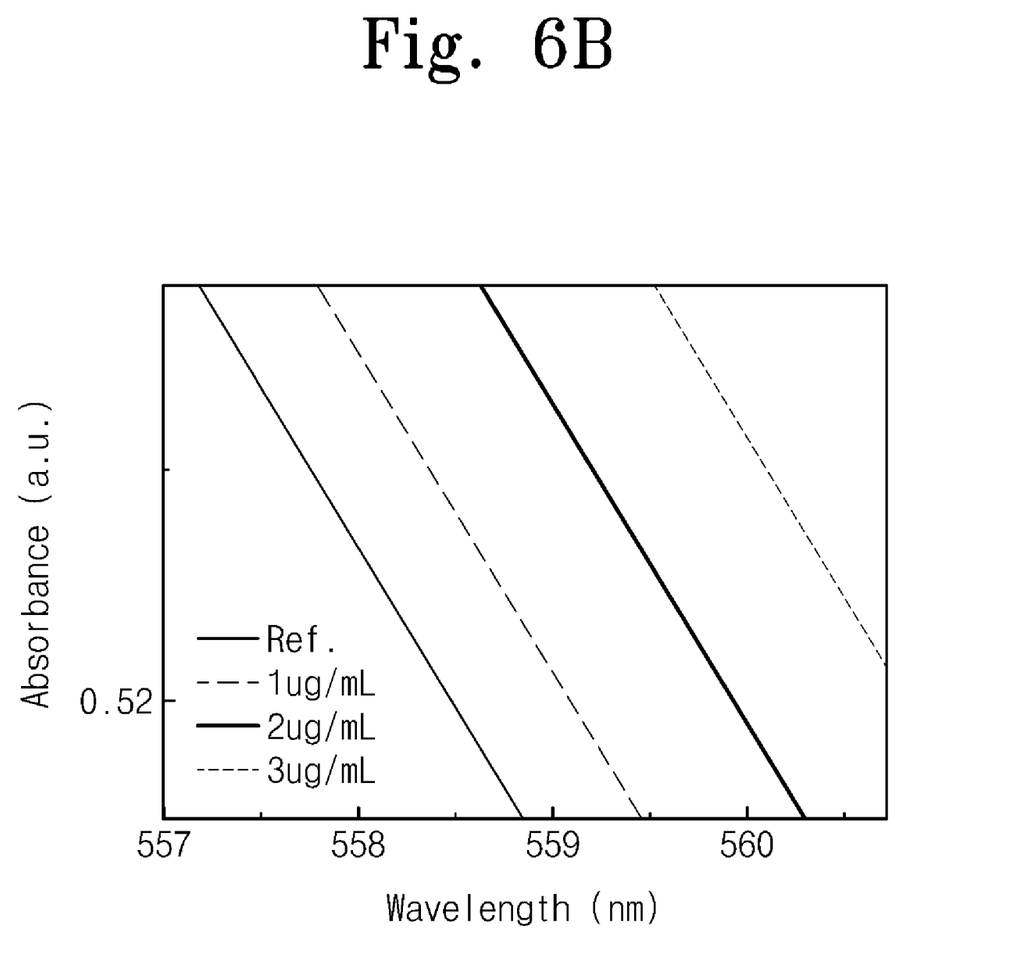
FIG. 6B is an enlarged graph of FIG. 6A.

FIG. 6A is a graph illustrating a change of a resonance wavelength according to a concentration change of target molecules supplied to a substrate in another embodiment of the present invention, and FIG. 6B is an enlarged graph of FIG. 6A.

FIGS. 6A and 6B graphs showing a resonance wavelength when only the gold nanoparticles to which the polyclonal albumin antibodies are immobilized are immobilized to the substrate and resonance wavelengths measured using the UV spectrometer when the albumin having concentrations of about 1 µg/mL, 2 µg/mL, and 3 µg/mL are provided respectively.

Referring to FIGS. 6A and 6B, as the concentration of the albumin increases, the resonance wavelength of the emission light emitted from the surfaces of the gold nanoparticles is moved. Particularly, when the concentration of the albumin increases by about µg/mL, the resonance wavelength is moved toward a right side within a range of less than about 1 nm. Thus, the resonance wavelength of the emission light emitted from the surfaces of the gold nanoparticles may be measured to quantify the concentration of the albumin.

According to the apparatus for detecting the biomaterials and the method for detecting the biomaterials using the same, the change of the surface plasmon resonance wavelength can be detected from the surfaces of the metal nanoparticles to analyze the biomaterials. Also, the apparatus for detecting the biomaterials can be miniaturized using the metal nanoparticles of nano-size.

In addition, since the metal nanoparticles having a spherical shape are used, when the incident light for generating the surface plasmon resonance is irradiated, the surface plasmon resonance phenomenon may occur on the surfaces of the metal nanoparticles without reference to the incident angle of the incident light. Thus, the biomaterial can be easily detected.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An apparatus for detecting biomaterials, comprising:
    a light source unit providing incident light;
    a biomaterial reacting unit comprising a substrate and metal nanoparticles spaced from the substrate; and
    a detection unit detecting a resonance wavelength of emission light emitted from the metal nanoparticles by a surface plasmon resonance phenomenon,
    wherein the surface plasmon resonance phenomenon is induced on surfaces of the metal nanoparticles by the incident light, and first detecting molecules specifically binding to target molecules are immobilized to the surfaces of the metal nanoparticles.

2. The apparatus of claim 1, wherein the metal nanoparticles are spaced from the substrate and have fluidity.

3. The apparatus of claim 1, wherein the biomaterial reacting unit comprises a buffer solution in which the metal nanoparticles are dispersed.

4. The apparatus of claim 1, further comprising blocking molecules on the surfaces of the metal nanoparticles between the immobilized first detecting molecules.

5. The apparatus of claim 1, wherein the metal nanoparticles are formed of gold (Au), silver (Ag), chrome (Cr), nickel (Ni), or titanium (Ti).

6. The apparatus of claim 1, wherein the first detecting molecules comprise an albumin antibody, an anti-prostate specific antigen (anti-PSA) antibody, an N-telopeptide antibody, or a deoxy-pyridinoline (DPD) antibody.

7. The apparatus of claim 1, wherein the detection unit comprises an ultraviolet (UV) spectrometer.

8. The apparatus of claim 1, further comprising second detecting molecules immobilized to a surface of the substrate of the biomaterial reacting unit, the second detecting molecules specifically binding to the target molecules.

9. The apparatus of claim 8, wherein the first detecting molecules comprise monoclonal antibodies, and the second detecting molecules comprise polyclonal antibodies.

10. The apparatus of claim 8, wherein the second detecting molecules are immobilized to the surface of the substrate by a carboxyl group (—COOH), a thiol group (—SH), a hydroxyl group (—OH), a silane group, amine group, or an epoxy group.

11. A method for detecting biomaterials, the method comprising:
    immobilizing first detecting molecules to surfaces of metal nanoparticles having fluidity;
    irradiating incident light onto the metal nanoparticles to induce a surface plasmon resonance phenomenon and detect a first resonance wavelength of emission light emitted from the metal nanoparticles;
    specifically binding target molecules to the first detecting molecules immobilized to the metal nanoparticles;
    irradiating the incident light onto the metal nanoparticles to which the target molecules are immobilized to induce the surface plasmon resonance phenomenon and detect a second resonance wavelength of the emission light emitted from the metal nanoparticles; and comparing the first resonance wavelength to the second resonance wavelength to analyze the target molecules.

12. The method of claim 11, wherein the immobilizing of the first detecting molecules comprises:

preparing a buffer solution in which the metal nanoparticles are dispersed; and supplying the first detecting molecules to the buffer solution to immobilize the first detecting molecules to surfaces of the metal nanoparticles.

13. The method of claim 12, wherein the first detecting molecules are immobilized to the surfaces of the metal nanoparticles by chemical adsorption, covalent-binding, electrostatic attraction, copolymerization, or avidin-biotin affinity system.

14. The method of claim 12, after the immobilizing of the first detecting molecules, further comprising supplying blocking molecules into the buffer solution to immobilize the blocking molecules to the surfaces of the metal nanoparticles between the immobilized first detecting molecules.

15. The method of claim 11, wherein the analyzing of the target molecules comprises detecting variation between the first resonance wavelength and the second resonance wavelength to quantify a concentration of the target molecules.

16. The method of claim 11, wherein the metal nanoparticles are formed of gold (Au), silver (Ag), chrome (Cr), nickel (Ni), or titanium (Ti).

17. The method of claim 11, wherein the first detecting molecules comprise an albumin antibody, an anti-prostate specific antigen (anti-PSA) antibody, an N-telopeptide antibody, or a deoxy-pyridinoline (DPD) antibody.

18. A method for detecting biomaterials, the method comprising:

preparing a buffer solution in which metal nanoparticles to which first detecting molecules are immobilized are dispersed;

preparing a substrate to which second detecting molecules are immobilized to a surface thereof;

specifically binding target molecules to the second detecting molecules;

supplying the buffer solution to the substrate to specifically bind the target molecules to the first detecting molecules;

irradiating incident light onto the metal nanoparticles to induce a surface plasmon resonance phenomenon; and detecting a resonance wavelength of emission light emitted from the metal nanoparticles by the surface plasmon resonance phenomenon and varied according to the specific binding between the target molecules and the first detecting molecules.

19. The method of claim 18, wherein existence of the target molecules is determined according to the resonance wavelength of the emission light.

20. The method of claim 18, wherein the first detecting molecules comprise polyclonal antibodies, and the second detecting molecules comprise monoclonal antibodies.

* * * * *